United States Patent [19]
Lampotang et al.

[11] Patent Number: 5,887,611
[45] Date of Patent: Mar. 30, 1999

[54] GAS BLENDER

[75] Inventors: Samsun Lampotang; Richard Joel Melker, both of Gainesville; Paul B. Blanch, Alachua, all of Fla.; Aneel Rijhwani, Palatine, Ill.

[73] Assignee: The University of Florida, Gainesville, Fla.

[21] Appl. No.: 775,302

[22] Filed: Dec. 31, 1996

[51] Int. Cl.[6] .................................................. G05D 11/13
[52] U.S. Cl. ........................................ 137/93; 137/101.19
[58] Field of Search .......................... 137/88, 93, 101.19

[56] References Cited

U.S. PATENT DOCUMENTS

| | | | |
|---|---|---|---|
| 3,593,735 | 7/1971 | Reiher | 137/88 |
| 3,856,033 | 12/1974 | Strain et al. | 137/93 X |
| 4,236,546 | 12/1980 | Manley et al. | 137/93 X |
| 4,345,610 | 8/1982 | Herter et al. | 137/88 X |
| 4,379,460 | 4/1983 | Judell | 128/671 |
| 4,444,201 | 4/1984 | Itoh | 128/716 |
| 4,506,678 | 3/1985 | Russell et al. | 128/723 |
| 4,565,194 | 1/1986 | Weerda et al. | 128/204.23 |
| 4,602,653 | 7/1986 | Ruiz-Vela et al. | 137/88 |
| 4,757,824 | 7/1988 | Chaumet | 128/716 |
| 4,781,201 | 11/1988 | Wright et al. | 128/671 |
| 4,813,431 | 3/1989 | Brown | 128/748 |
| 4,838,259 | 6/1989 | Gluck et al. | 128/201.21 |
| 4,928,684 | 5/1990 | Brietenfelder et al. | 128/204.21 |
| 4,972,842 | 11/1990 | Korten et al. | 128/716 |
| 5,014,694 | 5/1991 | De Vries et al. | 128/205.24 |
| 5,107,831 | 4/1992 | Halpern et al. | 128/204.26 |
| 5,127,400 | 7/1992 | De Vries et al. | 128/205.24 |
| 5,161,525 | 11/1992 | Kimm et al. | 128/204.26 |
| 5,307,795 | 5/1994 | Whitwam et al. | 128/204.25 |
| 5,316,009 | 5/1994 | Yamada | 128/716 |
| 5,390,666 | 2/1995 | Kimm et al. | 128/204.26 |
| 5,396,893 | 3/1995 | Oberg et al. | 128/671 |
| 5,429,123 | 7/1995 | Shaffer et al. | 128/204.23 |
| 5,494,028 | 2/1996 | De Vries et al. | 128/205.24 |
| 5,540,251 | 7/1996 | Mayeaux | 137/88 |
| 5,546,935 | 8/1996 | Champeau | 128/205.23 |

FOREIGN PATENT DOCUMENTS 0482261  4/1992  European Pat. Off. .

Primary Examiner—Stephen M. Hepperle
Attorney, Agent, or Firm—Needle & Rosenberg, P.C.

[57] ABSTRACT

A gas blender comprising a plenum for mixing gases, at least one flow valve, an oxygen sensor, a microprocessor, and driver circuits. The inlet gas port is adapted to be in fluid communication with a supply of a desired gas and the flow valve is disposed between the supply of gas and the inlet of the plenum. At least one driver circuit adjusts the flow valves to change the gas flow rate therethrough and, accordingly, the rate at which gas enters into the plenum. The oxygen sensor measures the percentage composition of oxygen exiting from, or inside, the plenum and generates an output based on the measured percentage composition of oxygen. The microprocessor controls the percentage composition of oxygen exiting from the plenum and is electrically coupled to the output of the oxygen sensor. The microprocessor compares the output of the oxygen sensor to a predetermined level of oxygen and generates a response signal based on the comparison, which is communicated to the driver circuits. The driver circuits are electrically coupled to both the microprocessor and the flow valves and adjust the flow valve so that the percentage composition of oxygen exiting the plenum is maintained at the predetermined level. The blender of the present invention may also include a pressure sensor in fluid communication with the outlet of the plenum.

15 Claims, 4 Drawing Sheets

GAS BLENDER

BACKGROUND OF THE INVENTION

1. Field of the Invention

The present invention relates to blending of gases and, more particularly, to respiratory care and to a gas blender that mixes gases, monitors the mixed gases, and controls the mixed gases so that the gases are maintained at the desired levels, e.g., at a selected concentration content and gas pressure.

2. Background Art

Oxygen therapy is used to treat patients suffering from respiratory diseases. Many of these patients need higher fractions of inspired oxygen ($F_IO2$) than exist in air (21% oxygen) to obtain sufficient oxygenation to their tissues. Oxygen therapy is of particular value in dealing with respiratory diseases resulting from inadequate ventilation and cases of hypoxemia, which is a relative deficiency of oxygen in the arterial blood. In clinical practice, arterial oxygen is quantified by measurement of the partial pressure exerted by the oxygen dissolved in plasma (PaO2). As a result, hypoxemia potentially affects the normal physiologic processes by increasing the cardiopulmonary work and impairing the maintenance of tissue oxygenation. Therefore, as research indicates, breathing a gas mixture with an increased $F_IO2$ may correct the hypoxemia and reduce the respiratory work required to maintain a given PaO2.

Ventilation is the process of delivering oxygen to and washing carbon dioxide from the alveoli in the lungs. The movement of gas in the respiratory tract is tidal (to-and-fro) since the tract dead-ends in the alveoli and has only one outlet for gas to be exhaled from the system. Patients requiring oxygen therapy may also require mechanical ventilation due to respiratory failure. In these instances, a variety of mechanical ventilators is available. Most modern ventilators allow the clinician to select and use several modes of inhalation either individually or in combination. These modes can be defined in three broad categories: spontaneous, assisted, or controlled. During spontaneous ventilation without other modes of ventilation, the patient breathes at his own pace, but other interventions may affect other parameters of ventilation including, the tidal volume and raising the baseline pressure above ambient to improve oxygenation.

In assisted ventilation, the patient initiates the inhalation by lowering the baseline pressure to varying degrees, and then the ventilator "assists" the patient in completing the breath by the application of positive pressure. During controlled ventilation, the patient is unable to breathe spontaneously or initiate a breath, and is therefore dependent on the ventilator for every breath. During spontaneous or assisted ventilation, the patient is required to "work" (to varying degrees) by using the respiratory muscles in order to breathe. During controlled ventilation no work is required of the patient. Modern ventilators are designed to minimize or control the work required of the patient in the spontaneous or assisted modes. The work required by the patient is generally referred to as work of breathing and can be measured and quantified in Joules/breath or Joules/L of ventilation.

One of the main goals in treating patients suffering from respiratory disorders is to reduce the respiratory work. Research indicates that a low resistance breathing system that allows high gas flow rates on demand during spontaneous inhalation usually meets the requirement. As mentioned above, many modern ventilators are designed to minimize respiratory work. However, many require the serial connection of a gas blender between the gas supplies and the ventilator to provide the proper gas mixture to obtain the selected $F_IO2$. Failure to have a blender capable of meeting the demands of the patient can compromise the effectiveness of the ventilator and consequently the health of the patient. At present many ventilators have "integral" blenders which may or may not meet the demand of the patient. Other ventilators presently rely on mechanical "stand alone" blenders which have been shown to have limited ability to meet the demands of the patient. Desirable characteristics of air/oxygen blenders used to produce high flow on demand are (1) a high-flow output greater than 120 liters/minute and (2) supply an approximately 50 pound per square inch gauge ("psig") output pressure.

Oxygen therapy may also have an adverse effect, especially if the $F_IO2$ is not carefully controlled to the needs of the patient. One example is "absorption atelectasis," in which increases in alveolar oxygen concentration due to excessive $F_IO2$ results in a reduction of the alveolar partial pressure of nitrogen. In alveoli with reduced ventilation but good perfusion, the volume of oxygen removed by the blood may be greater than the volume of gas that enters with each tidal ventilation. In this case, reduction of nitrogen partial pressure may allow the alveolar volume to decrease below a critical level, resulting in partial or complete collapse of the alveolus. The higher the $F_IO2$, the greater the degree of denitrogenation and the more likely the presence of absorption atelectasis.

Another adverse effect of oxygen therapy is oxygen toxicity. The inherent toxicity of oxygen to the tissue was demonstrated almost a century ago. Intracellular oxygen metabolism involves the serial reduction of oxygen to water, a process that involves the formation of highly reactive free radicals, superoxide molecules ($H_2O_2$) and hydroxyl ions (OH). These free radicals are capable of unregulated reactions with organic molecules that can result in damage to cell membranes and mitochondria and inactivation of cytoplasmic and nuclear enzymes. Therefore, oxygen toxicity is a potential problem in patients of any age.

It should be clear that an oxygen blender that can precisely and predictably maintain a selected $F_IO2$ is indispensable in the care of patients with pulmonary diseases and respiratory failure.

Unfortunately, most stand-alone and some integral medical gas blenders used to control $F_IO2$ have serious drawbacks, such as no or inadequate monitoring and correction safeguards. Accordingly, use of these prior art blenders may result in adverse effects during oxygen therapy. At present, all stand-alone blenders are entirely pneumatic and do not generate or react to any electrical signals. Therefore, the aforementioned stand-alone blenders are difficult to interface with computer controlled ventilators or other electronic medical equipment that currently exist. The prior art pneumatic blenders also suffer from inadequate peak flow rates and output pressure dropout.

Another problem is that the prior art blenders are dedicated to only two gases. That is, the blender's components are configured to accept only air and oxygen. For example, if helium and oxygen need to be mixed, tedious re-calibration and replacement of the oxygen/air dial by a homemade oxygen/helium dial is required.

The Bird blender is probably the best known prior art blender and, like other prior art devices, is pneumatic. The blender uses a balance module and a proportioning module to provide mixing of air and oxygen. The nominally 50 psig air and oxygen gas sources (usually 40–60 psig) enter through the respective inlet connectors. Each connector incorporates a filter to trap impurities. From the filter, the gases travel through a duckbill check valve which prevents possible reverse flow from either the air or oxygen supply systems. The two gases next enter a balance module to equalize the operating pressure of the air and oxygen gases before entering the proportioning module.

The gases then each flow into the proportioning module and mix according to the oxygen percentage selected by the control knob. This module consists of a double ended needle valve positioned between two valve seats. Of the two valve seats, one valve seat controls the passage of air and one valve seat controls the passage of oxygen into the blender outlet. At the outlet, the two gases have been blended according to the oxygen percentage selected on the control knob. With the blender control knob at the 21% oxygen position, the double ended needle valve will completely block the flow of oxygen allowing only air to flow. By adjusting the control knob at the 100% oxygen position, the flow of air is blocked permitting only the flow of oxygen to the gas outlets of the blender.

There are two gas outlets in the Bird blender: a primary outlet and an auxiliary outlet. The primary gas outlet is used for unmetered high flow applications in the range of 15–120 liters/minute The auxiliary outlet is designated to deliver metered gas through a flowmeter. Mixed gas may accurately be delivered from this outlet at 2 liters/minute and above. With the auxiliary outlet operational, there is a minimal bleed flow (10–12 liters/minute) from this outlet.

The Bird blender has other significant limitations. Low peak flow rates is one. As previously mentioned, a primary goal in treating patients suffering from respiratory disorders is to reduce the respiratory work. Thus, it is desirable for a low resistance breathing system to provide high gas flow rates on demand during spontaneous inhalation. Research indicates that a high flow output greater than 150 liters/minute is desirable from an air/oxygen blender. It appears that supporting patients with a high flow demand system for spontaneous breathing reduces inspiratory effort and therefore diminishes work of breathing. This effect is likely attributable to the fact that some patients may have instantaneous flow demands up to 200 liters/minute. A ventilator with a peak spontaneous flow rate capability of 80–100 liters/minute may not meet some patients' spontaneous flow rate requirements. Such patients may become agitated, diaphoretic (perspire), and "fight the ventilator" in an effort to achieve a sufficient flow demand. The selection of 150 liters/minute as a desirable minimum peak flow rate for a blender is based on clinical observations that low flow rates can be insufficient, but 150 liters/minute is almost always adequate. The Bird blender can deliver a maximum flow rate of 120 liters/minute only momentarily under ideal conditions of 60% $F_IO2$ (1:1 mixture of air and oxygen) and 55 psig gas supply pressures. Peak flow rates of 90–100 liters/minute are achievable at other $F_IO2$ settings.

The Bird blender has an open loop design and also lacks any means of self-monitoring. Without a built-in oxygen sensor, the blender cannot correct itself, or even provide an alarm, if delivered $F_IO2$ is significantly different from the set $F_IO2$.

The constant bleed flow of 12 liters/minute from the auxiliary outlet is wasteful. The auxiliary outlet is used for low flow rate applications requiring metered flow. When a flowmeter is connected to the auxiliary outlet, a constant flow of gas (10–12 liters/minute) bleeds from the main outlet of the blender to atmosphere and is lost.

Thus, there is a need in the art for a blender that overcomes the problems that exist with the prior art devices. The blender should be electric or otherwise compatible with other equipment instead of being entirely pneumatic.

A need also exists in the art for a blender that is self-monitoring for oxygen content and, if desired, gas pressure. This monitoring is essential because of the potential adverse consequences that may arise if the gases delivered to the patient are not carefully controlled. An associated need in the art is for a feedback system to correct any variations that exists between the desired/set and actual gas content and pressure.

Still another need in the art is for a blender that provides better flow control. It is also desired that the blender be designed to provide high peak flow rates for those applicable situations.

Yet another need in the art is for a blender that can use gases other than oxygen and air with out requiring a major reconfiguration of the blender components.

SUMMARY OF THE INVENTION

The above needs in the prior art are met by the present invention, which is an improved gas blender. One preferred embodiment comprises a plenum for mixing gases having a plurality of inlet gas ports and an outlet gas port, at least one flow valve, an oxygen sensor, a microprocessor, and driver circuits.

Each flow valve defines a passage through which a gas traverses and each flow valve is disposed adjacent to and in fluid communication with one respective inlet gas port of the plenum. The inlet gas port is adapted to be in fluid communication with a supply of a desired gas and the flow valve is disposed between the supply of gas and the inlet gas port.

The present invention also includes at least one flow controlling means for adjusting the passage of the flow valves. Each flow controlling means opens or closes the passage of one flow valve to change the gas flow rate therethrough and, accordingly, the rate that gas enters into the plenum.

The oxygen sensor is disposed in fluid communication with the outlet gas port of the plenum and measures the percentage of oxygen exiting from the plenum. The oxygen sensor generates an output based on the measured percentage composition of oxygen.

The microprocessor controls the percentage composition of oxygen exiting from the plenum. The microprocessor is electrically coupled to the output of the oxygen sensor and compares the output of the oxygen sensor to a predetermined level of oxygen, which is the level that the clinician sets. The microprocessor generates a response signal based on the comparison, which is communicated to the driver circuits, described below.

The driver circuits are electrically coupled to both the microprocessor and the flow control means. The driver circuits adjust at least one of the flow control means so that the percentage composition of oxygen in fluid communication with the output port of the plenum is maintained at the predetermined level. For example, if the present invention is connected to a supply of oxygen and air, the predetermined oxygen level is 30%, and the oxygen detector detects the oxygen level at 25%, the microprocessor would direct the flow control means via the driver circuits to open the passage of the oxygen flow valve relative to the other passage in the other flow valve. The oxygen detector continuously monitors the oxygen level ensuring that it reaches and maintains the 30% level.

The blender of the present invention may also include a pressure sensor in fluid communication with the outlet gas port of the plenum. Similar to the oxygen detector, the pressure sensor generates an output based on the pressure of the gases exiting the plenum. The microprocessor is electrically coupled with and responsive to the output of the pressure sensor so that the microprocessor compares the output of the pressure sensor to a predetermined pressure and generates a response signal based on the comparison. If the output pressure of the gases is not at the predetermined pressure, the driver circuits adjust at least one flow controlling means in response to a signal from the microprocessor so that the pressure of the gases exiting from the plenum is established and maintained at the predetermined pressure.

An advantage of the present invention is that the operating steps occur continuously when the mixed gases are being directed to the patient. In contrast, the prior art devices do not allow continuous monitoring and correction because they are pneumatic and will not interface with signals of a sensing device, such as an oxygen or pressure sensor. This monitoring is essential because of the potential adverse consequences that may arise if the gases delivered to the patient are not carefully controlled.

Unlike prior art pneumatic blenders that suffer from certain drawbacks, such as inadequate peak flow rates, proportional flow control valves that are controlled by an 80535 microcontroller programmed in the C language are used to deliver the desired air and oxygen flow rates. The present invention also provides improved control of flow rate compared to the prior art.

The microcontroller in the present invention allows the use of any second gas (or even any first gas, although it is usually oxygen in medical applications) without the addition or modification of any components. The calibration curve for the valve controlling the alternative second gas can be pre-programmed into the control software and the clinician could select the nature of the alternative second gas from a user interface.

The peak flow rate capability of the present invention is 180 liters/minute with an acceptable pressure drop of 5 psig between the input pressure and the output pressure of the blender, which is the output pressure drop.

One embodiment of the electronic gas blender of the present invention can also be completely integrated into a currently existing electronic ventilator.

DETAILED DESCRIPTION OF THE INVENTION

The present invention is more particularly described in the following examples that are intended as illustrative only since numerous modifications and variations therein will be apparent to those skilled in the art. As used in the specification and in the claims, "a" can mean one or more, depending upon the context in which it is used.

Figure 1:
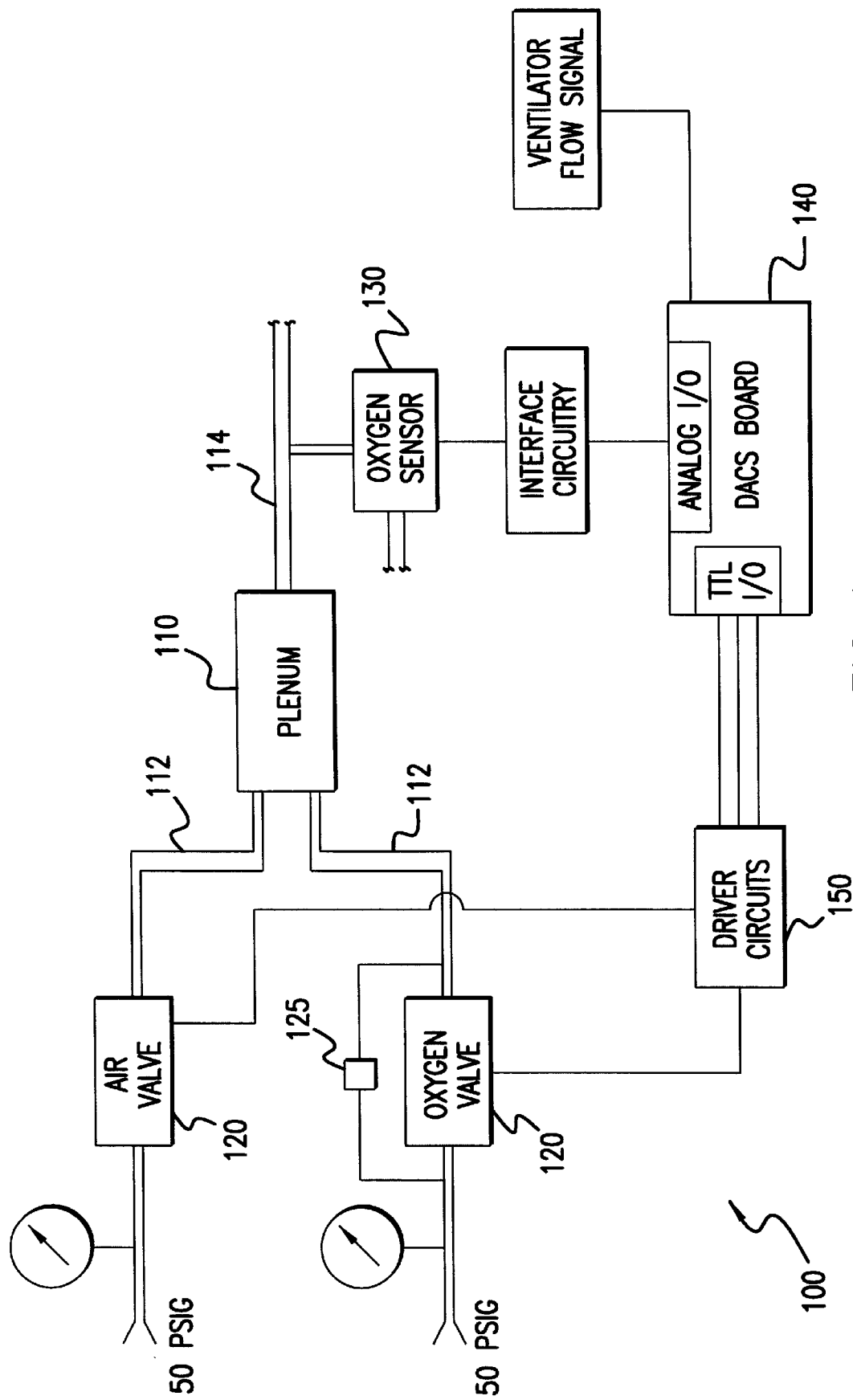
FIG. 1 is a block diagram of a first embodiment of the present invention, in which the oxygen level is monitored and then used in a feedback loop to control the oxygen and air valves via the driver circuits.
Figure 3:
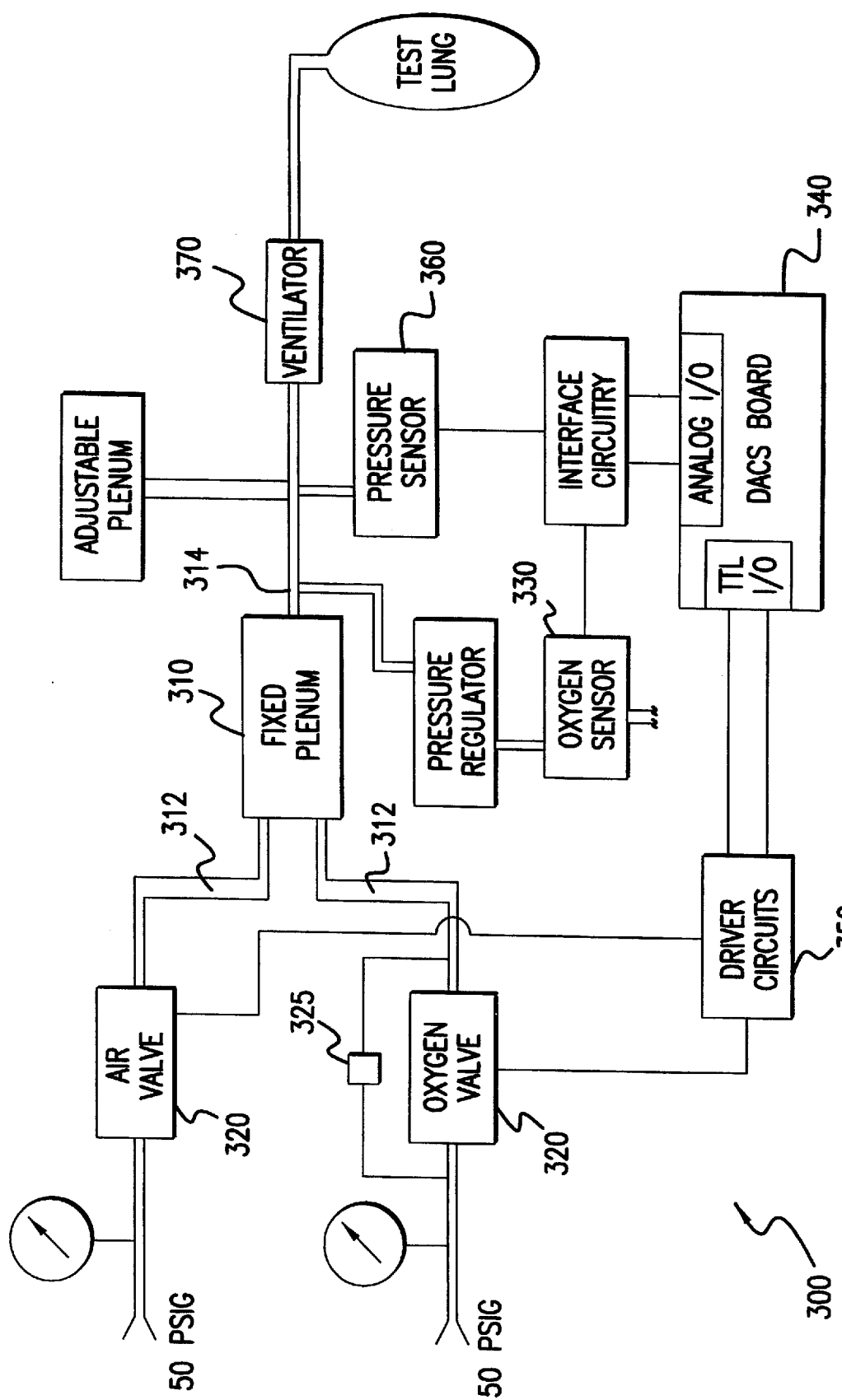
FIG. 3 is a block diagram of a second embodiment of the present invention, in which both the oxygen level and the output pressure are monitored and then used in a feedback loop to control the oxygen and air valves via the driver circuits.

Referring first to FIGS. 1 and 3, a first and a second embodiment of the present invention are shown, respectively, in which like components have like numbers. That is, a component in FIG. 1 has a 100 series number and the same component in FIG. 3 has a 300 series number, wherein the last two digits are identical for the same component. However, references to these components below only reference the 100 series number.

The present invention is a gas blender 100 that comprises a plenum 110 for mixing gases, a plurality of regulating means for adjusting gas flow rate into the plenum 110, a gas composition sensing and signal generating means for measuring the percentage composition of a desired gas exiting from the plenum 110, a comparing means for controlling the percentage composition of the desired gas exiting from the plenum 110, and a feedback means for adjusting at least one of the regulating means so that the percentage composition of the desired gas exiting the plenum 110 is maintained at a predetermined level. As one skilled in the art will appreciate, the reference to the gases exiting the plenum 110 can also be applicable to the inside of the plenum 110 at a location where the gases have mixed so that an accurate measurement of the percentage composition of the desired gas is obtained.

The plenum 110, or chamber for mixing gases, has a plurality of inlet gas ports 112 and an outlet gas port 114. Each inlet gas port 112 is adapted to be in fluid communication with a supply of a desired gas and the mixed gases exit from the outlet gas port 114. The plenum 110 can have multiple outlet gas ports 114 if, for example, the blender 100 supplies two or more devices such as a ventilator and the nebulizer of that ventilator.

Each of the plurality of regulating means for adjusting gas flow rate into the plenum 110 is disposed adjacent to and in fluid communication with one respective inlet gas port 112 of the plenum 110. Each regulating means is adapted to regulate the flow of the supply of gas in fluid communication with its respective inlet gas port 112. For example, usually one supply of gas is oxygen and the other supply of gas is either air, nitrogen, helium, nitrous oxide, nitric oxide, carbon dioxide, or a mixture thereof.

In the preferred embodiment, each regulating means comprises a flow valve 120 defining a passage (not shown) through which a gas traverses and a flow controlling means for adjusting the passage to change the rate of flow of the gas therethrough. The feedback means adjusts the flow controlling means of at least one flow valve 120, if necessary, so that the percentage composition of the desired gas exiting the plenum 110 through the outlet gas port 114 is established and maintained at the predetermined level. The flow valve 120 can be a binary valve, which is in either a fully open or a fully closed position, or, more preferably, a proportional valve, in which the passage is opened different amounts corresponding to various desired flow rates. Also, a normally closed bypass valve 125 is preferably included to circumvent the oxygen flow valve 120 to protect the patient in case of a power failure.

The gas composition sensing and signal generating means, which measures the percentage composition of a desired gas exiting from the plenum 110, is disposed in fluid communication with the outlet gas port 114 of the plenum 110 or inside the plenum 110 itself. The gas composition sensing and signal generating means generates an output based on the measured percentage composition of the desired gas, which usually will be the level of oxygen, but could be another gas if desired. Accordingly, the gas composition sensing and signal generating means preferably is an oxygen sensor 130.

The comparing means is responsive to the output of the gas composition sensing and signal generating means. The comparing means compares the output of the gas composition sensing and signal generating means to a predetermined level of the desired gas and generates a response signal based on the comparison. An example of the predetermined level of the desired gas is a setting of 30% oxygen, which is set by the clinician on the ventilator's user interface based on the patient's condition. Preferably, the comparing means comprises a microprocessor 140 electrically coupled to the oxygen sensor 130 used as the gas composition sensing and signal generating means.

The comparing means controls the percentage composition of the desired gas exiting from the plenum 110 by correcting the composition of the gases entering the plenum 110 through the inlet gas ports 112. This control occurs using the feedback means, which is responsive to the response signal of the comparing means. The feedback means adjusts at least one of the regulating means so that the percentage composition of the desired gas in fluid communication with the output port of the plenum 110 is maintained at the predetermined level.

Preferably, the feedback means comprises at least one driver circuit 150 electrically coupled to the microprocessor 140 and also electrically coupled to each regulating means, e.g., the flow controlling means. The driver circuits 150 adjust the regulating means based on electrical signals received from the microprocessor 140, thus varying the percentage composition of each gas received within the plenum 110.

Referring specifically to FIG. 1, the first embodiment of the present invention is an integrated gas blender designed to be integrated with an electronic ventilator. The ventilator's microcontroller calculates total flow demand, which is communicated from the ventilator to the integrated blender, and is therefore known at all times. The determined total flow demand is split up into the component air and oxygen flows according to the set $F_iO2$. For example, if the two supplied gases were oxygen and nitrogen (for ease of calculation because air contains 20% oxygen) and the ventilator's microcontroller requested a total flow rate of 100 liters/minute and the desired $F_iO2$ was 0.6, then the oxygen manifold would deliver 0.6*100=60 liters/minute and the second gas (nitrogen) manifold would deliver 40 liters/minute. Due to the large turndown ratio (highest flow rate/lowest flow rate) of each flow valve and the expected non-linear characteristics and inter-unit variance of the flow valve 120, the output mixture $F_iO2$ might be significantly different from the desired $F_iO2$. To correct this potential problem, an oxygen sensor 130 is used in a feedback loop to modify the ratio in which the total flow demand is split according to the error in $F_iO2$. The flow valves 120 are preferably controlled by an 80535 microcontroller programmed in the C language to deliver the desired air and oxygen flow rates.

Figure 2:
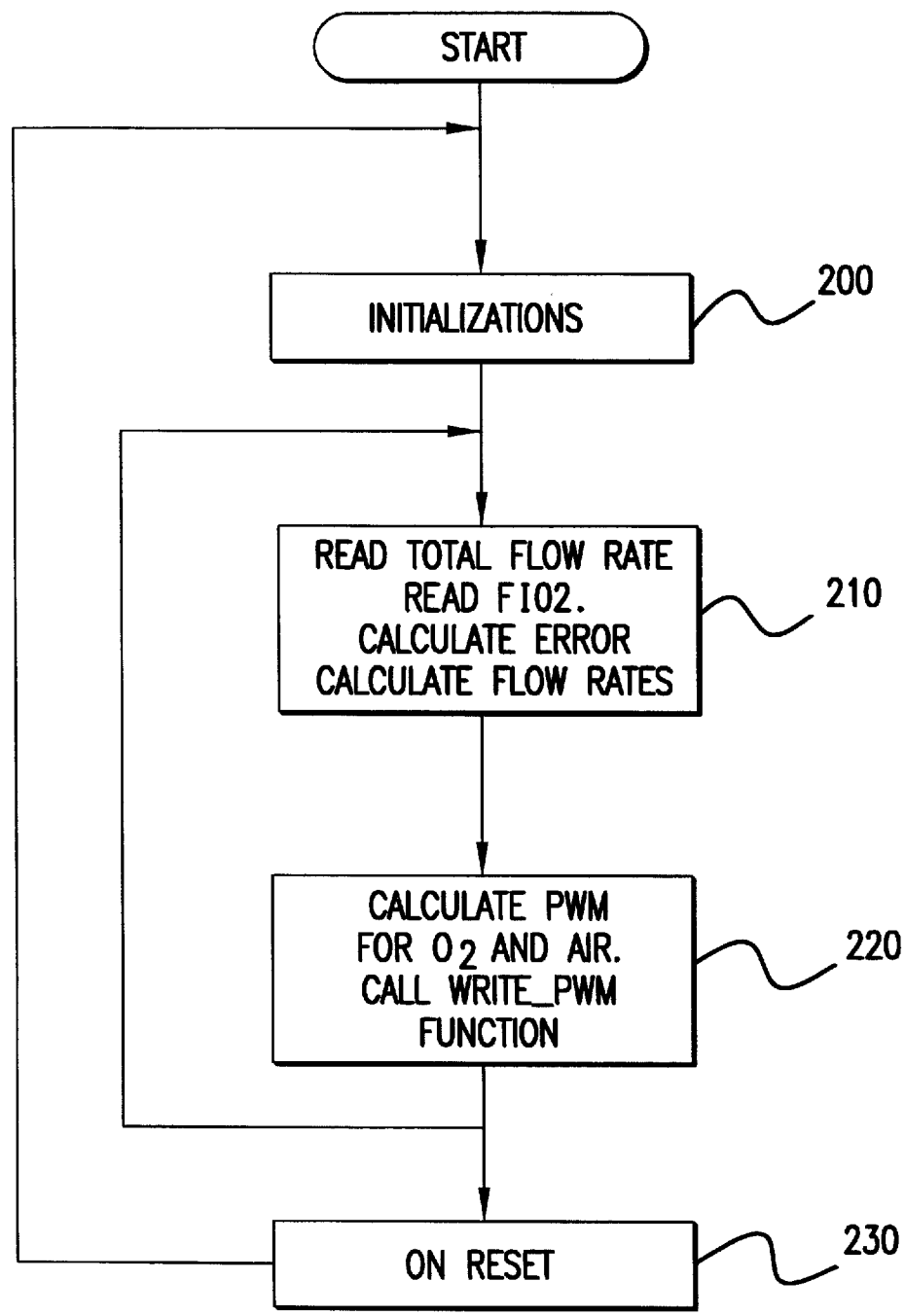
FIG. 2 is a flowchart for the control software for the first embodiment shown in FIG. 1.

FIG. 2 shows a flowchart for the proportional integral ("PI") digital control algorithm that controls the first embodiment of the present invention. The blender is initialized at step 200. At step 210, the total flow rate is read, the selected parameter is monitored (e.g., the inspired fraction of oxygen), the error is calculated between the selected parameter and the predetermined level, and the flow rate of the component gases is calculated. Then at step 220, the pulse width modulation for the air and oxygen valves is calculated and the software tries to maintain the inspired fraction of oxygen at the predetermined level. As one skilled in the art will appreciate, other methods instead of pulse width modulation can be used. The program continues to operate until it is reset at step 230. The maximum response time is preferably to obtain 90% of the desired change in $F_iO2$ in 90 seconds or less.

Referring now to FIG. 3, the second embodiment of the present invention is shown. This embodiment further comprises a gas output pressure sensing and signal generating means, which is disposed in fluid communication with the outlet gas port 314 of the plenum 310. The gas pressure sensing and signal generating means measures the output pressure of the gases exiting the plenum 310 through the outlet gas port 314 and generates an output based on the output pressure of the gases exiting the plenum 310. The comparing means is responsive to the output of the gas pressure sensing and signal generating means, similar to the gas composition sensing and signal generating means. The comparing means compares the output of the gas pressure sensing and signal generating means to a predetermined pressure and generates a response signal based on the comparison. Then, the feedback means adjusts at least one of the regulating means, if necessary, so that the output pressure of the gases exiting from the plenum 310 is maintained at the predetermined pressure. Thus, the feedback means, which is responsive to the response signal of the comparing means, adjusts at least one of the regulating means so that (1) the percentage composition of the desired gas in fluid communication with the output port of the plenum 310 is maintained at the predetermined level and (2) the output pressure of the gases exiting from the plenum 310 is maintained at the predetermined pressure. Preferably, in this embodiment the gas pressure sensing and signal generating means comprises a pressure sensor 360. Thus, the comparing means comprises a microprocessor 340 electrically coupled to both the oxygen sensor 330 and the pressure sensor 360.

The second embodiment, which is also known as a stand alone medical gas blender, is designed for use with any ventilator 370 (electronic or pneumatic). An example is a commercial ventilator (Siemens Servo Ventilator 900C, Solna, Sweden). The control software of the second embodiment does not interface with the ventilator's control software, if any exists. Therefore, the total flow rate demand from the ventilator is unknown. Pressure at the blender output will vary as the flow rate demand changes, e.g., as the flow rate demand increases, the blender output pressure will drop.

As discussed above for the first embodiment, only $F_iO2$ is monitored and controlled, since the flow rate is known from the ventilator's microcontroller software.

In the second embodiment, however, $F_iO2$ as well as output pressure are simultaneously monitored and controlled in real time to defined set points. The pressure sensor 360 is used as a second feedback loop that will modulate the total flow rate to maintain the output pressure. As will be noted, many components are similar to those for the first embodiment with the significant difference being a pressure sensor is included.

Figure 4:
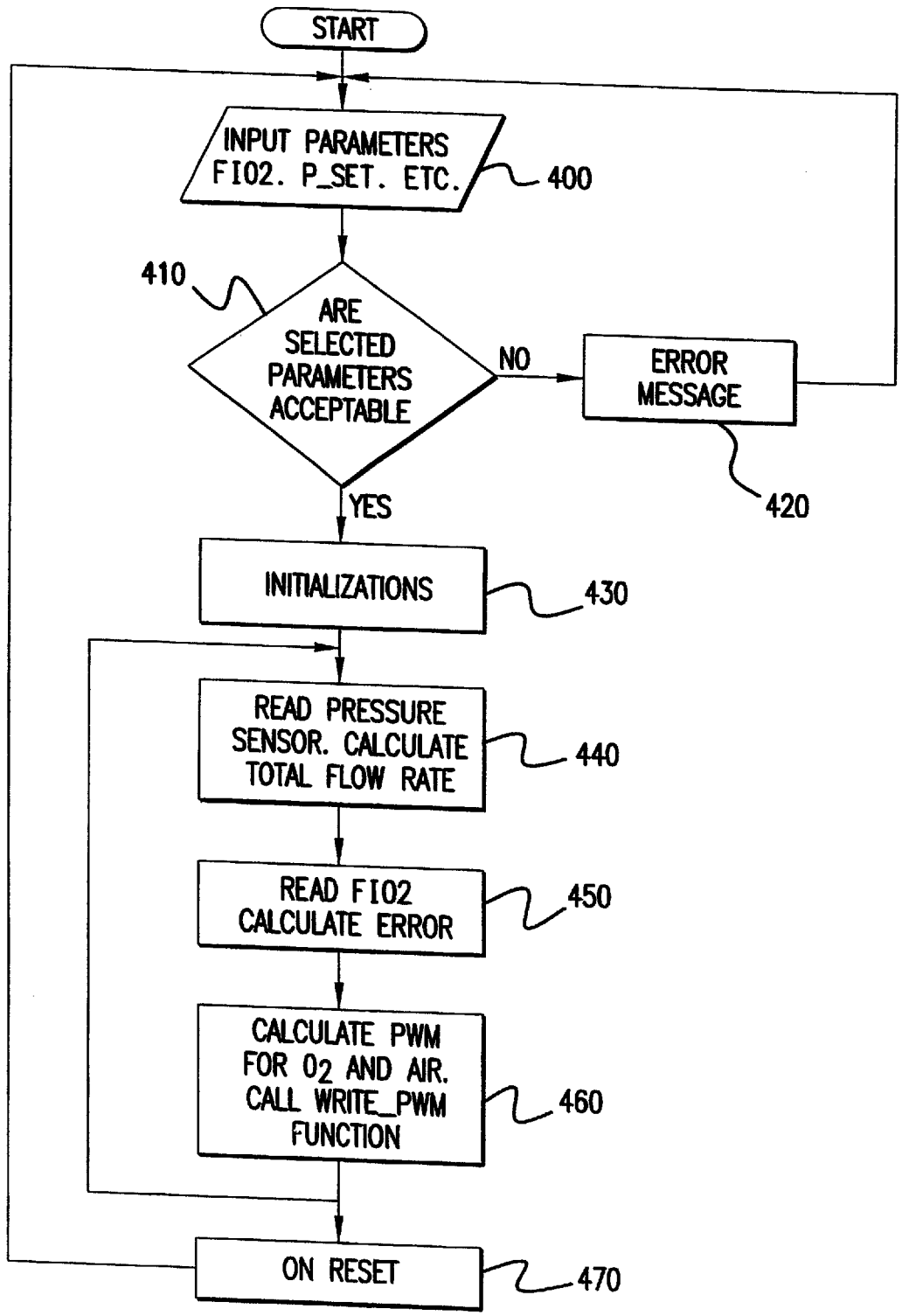
FIG. 4 is a flowchart for the control software for the second embodiment shown in FIG. 3.

FIG. 4 shows a flowchart for the software that controls the second embodiment of the present invention. The program, similar to the one for the first embodiment shown in FIG. 2, is another 'while' loop that continues to execute as long as the blender is not reset. At step 400, the input parameters are selected, such as the inspired fraction of oxygen, output pressure, etc. At step 410, the selected input parameters are checked to verify that they are acceptable. If the parameters are not acceptable, step 420 sends an error message that is displayed to warn the clinician of the problem. If the selected parameters are acceptable, then the blender is initialized at step 430. At step 440, the output pressure is monitored and the total flow rate of the gases is calculated. At step 450, the inspired fraction of oxygen is monitored and the error calculated. Then at step 460, the component flow rates, adding up to the total flow rate, are calculated and the control algorithm tries to maintain the inspired fraction of oxygen and output pressure at the predetermined levels. Depending on the set output pressure and inspired fraction of oxygen, the control algorithms in the program try to maintain the output pressure and inspired fraction of oxygen at their respective set points. The program continues to operate until it is reset at step 470. The maximum response time is preferably to obtain 90% of the desired change in both $F_IO2$ and output pressure in 90 seconds or less.

As one skilled in the art will appreciate, it is desirable to integrate the present invention with alarms. Examples include $F_IO2$ output outside a desired range, low and high output pressure, low and high inlet or supply pressures, and power failure. A normally closed bypass valve 325, which circumvents and is parallel to the oxygen valve 320, protects the patient during a power failure. The present invention can also be designed to have a default setting in case of power failure. Of course, it is desired to use a backup power supply, such as a battery.

Although the present invention has been described with reference to specific details of certain embodiments thereof, it is not intended that such details should be regarded as limitations upon the scope of the invention except as and to the extent that they are included in the accompanying claims.

What is claimed is:

1. A gas blender, comprising:
   a. a plenum for mixing gases having a plurality of inlet gas ports and an outlet gas port, each inlet gas port being adapted to be in fluid communication with a supply of a desired gas;
   b. a plurality of regulating means for adjusting gas flow rate into the plenum, each regulating means being disposed adjacent to and in fluid communication with one respective inlet gas port of the plenum so that each regulating means is adapted to regulate the flow of the supply of gas in fluid communication with the respective inlet gas port;
   c. gas composition sensing and signal generating means, disposed in fluid communication with the outlet gas port of the plenum, for measuring the percentage composition of a desired gas exiting from the plenum, wherein the gas composition sensing and signal generating means generates an output based on the measured percentage composition of the desired gas;
   d. a ventilator that generates a ventilator flow signal based on a total flow demand of the ventilator;
   e. comparing means for controlling the percentage composition of the desired gas exiting from the plenum, the comparing means being responsive to the ventilator flow signal of the ventilator and the output of the gas composition sensing and signal generating means, wherein the comparing means compares the output of the gas composition sensing and signal generating means to a predetermined level of the desired gas composition, evaluates the ventilator flow signal and generates a response signal based on the comparison; and
   f. feedback means, responsive to the response signal of the comparing means, for adjusting at least one of the regulating means so that the percentage composition of the desired gas in fluid communication with the output port of the plenum is maintained at the predetermined level.

2. The gas blender of claim 1, wherein each regulating means comprises:
   a. a flow valve defining a passage through which a gas traverses; and
   b. flow controlling means for adjusting the passage to change the rate of flow of the gas therethrough, wherein the feedback means adjusts the flow controlling means of at least one flow valve.

3. The gas blender of claim 1, wherein one supply of gas is oxygen and the other supply of gas comprises a selected one of air or nitrogen, and wherein the gas composition sensing and signal generating means comprises an oxygen sensor.

4. The gas blender of claim 3, wherein the comparing means comprises a microprocessor electrically coupled to the oxygen sensor.

5. The gas blender of claim 4, wherein the feedback means comprises at least one driver circuit electrically coupled to the microprocessor and also electrically coupled to each regulating means, wherein the driver circuits adjust the regulating means based on electrical signals received from the microprocessor, thereby varying the percentage of each gas received within the plenum.

6. The gas blender of claim 1, further comprising a gas pressure sensing and signal generating means, disposed in fluid communication with the outlet gas port of the plenum, for measuring pressure, wherein the gas pressure sensing and signal generating means generates an output based on the pressure of the gases exiting the plenum, wherein the comparing means is responsive to the output of the gas pressure sensing and signal generating means so that the comparing means compares the output of the gas pressure sensing and signal generating means to a predetermined pressure and generates a response signal based on the comparison, and wherein the feedback means adjusts at least one of the regulating means so that the pressure of the gases exiting from the plenum is maintained at the predetermined pressure.

7. A gas blender, comprising:
   a. a plenum for mixing gases having a plurality of inlet gas ports and an outlet gas port, each inlet gas port being adapted to be in fluid communication with a supply of a desired gas;
   b. a plurality of regulating means for adjusting gas flow rate into the plenum, each regulating means being disposed adjacent to and in fluid communication with one respective inlet gas port of the plenum so that each regulating means is adapted to regulate the flow of the supply of gas in fluid communication with the respective inlet gas port;
   c. gas composition sensing and signal generating means, disposed in fluid communication with the outlet gas port of the plenum, for measuring the percentage composition of a desired gas exiting from the plenum, wherein the gas composition sensing and signal generating means generates an output based on the measured percentage composition of the desired gas;

d. a gas pressure sensing and signal generating means, disposed in fluid communication with the outlet gas port of the plenum, for measuring the pressure of the gases exiting the plenum, wherein the gas pressure sensing and signal generating means generates an output based on the pressure of the gas exiting the plenum;

e. comparing means for controlling the percentage composition of the desired gas exiting from the plenum and for controlling the pressure of the gases exiting from the plenum, the comparing means being responsive to the output of the gas composition sensing and signal generating means, wherein the comparing means compares the output of the gas composition sensing and signal generating means to a predetermined level of the desired gas and generates a response signal based on the comparison, and wherein the comparing means is responsive to the output of the gas pressure sensing and signal generating means so that the comparing means compares the output of the gas pressure sensing and signal generating means to a predetermined pressure and generates a response signal based on the comparison; and f. feedback means, responsive to the response signal of the comparing means, for adjusting at least one of the regulating means so that the percentage composition of the desired gas in fluid communication with the output port of the plenum is maintained at the predetermined level and the pressure of the gases exiting from the plenum is maintained at the predetermined pressure.

8. The gas blender of claim 7, wherein each regulating means comprises:

a. a flow valve defining a passage through which a gas traverses; and b. flow controlling means for adjusting the passage to change the rate of flow of the gas therethrough, wherein the feedback means adjusts the flow controlling means of at least one flow valve.

9. The gas blender of claim 7, wherein one supply of gas is oxygen and the other supply of gas is a selected one of air or nitrogen, wherein the gas composition sensing and signal generating means comprises an oxygen sensor, and wherein the gas pressure sensing and signal generating means comprises a pressure sensor.

10. The gas blender of claim 9, wherein the comparing means comprises a microprocessor electrically coupled to both the oxygen sensor and the pressure sensor.

11. The gas blender of claim 10, wherein the feedback means comprises at least one driver circuit electrically coupled to the microprocessor and to each regulating means, wherein the driver circuits adjust the regulating means based on electrical signals received from the microprocessor, thereby varying the composition and pressure of the gases received within the plenum.

12. A gas blender, comprising:

a. a plenum for mixing gases having a plurality of inlet gas ports and an outlet gas port, each inlet gas port being adapted to be in fluid communication with a supply of a desired gas;

b. at least one flow valve, each flow valve defining a passage through which a gas traverses, each flow valve being disposed adjacent to and in fluid communication with one respective inlet gas port of the plenum;

c. at least one flow controlling means for adjusting the passage of the flow valves, each flow controlling means being adapted to adjust the passage of one flow valve to change the gas flow rate therethrough;

d. an oxygen sensor, disposed in fluid communication with the outlet gas port of the plenum, for measuring the percentage composition of oxygen exiting from the plenum, wherein the oxygen sensor generates an output based on the measured percentage composition of oxygen;

e. a ventilator that generates a ventilator flow signal based on a total flow demand of the ventilator; and f. a microprocessor for controlling the percentage composition of oxygen exiting from the plenum, the microprocessor being electrically coupled to the output of the oxygen sensor and receiving the ventilator flow signal from the ventilator, wherein the microprocessor compares the output of the oxygen sensor to a predetermined level of oxygen, evaluates the ventilator flow signal, generates a response signal based on the comparison and communicates the response signal to at least one of the flow control means so that the percentage of oxygen in fluid communication with the output port of the plenum is maintained at the predetermined level.

13. The gas blender of claim 12, wherein supplies of two different gases are adapted to be connected to two respective inlet gas ports of the plenum, wherein one supply of gas is oxygen and the other supply of gas is a selected one of air or nitrogen.

14. The gas blender of claim 12, further comprising a pressure sensor in fluid communication with the outlet gas port of the plenum, wherein the pressure sensor generates an output based on the pressure of the gases exiting the plenum, wherein the microprocessor is electrically coupled with and responsive to the output of the pressure sensor so that the microprocessor compares the output of the pressure sensor to a predetermined pressure and generates a response signal based on the comparison, and wherein the driver circuits adjust at least one flow controlling means in response to a signal from the microprocessor so that the pressure of the gases exiting from the plenum is maintained at the predetermined pressure.

15. A gas blender, comprising:

a. a plenum for mixing gases having a plurality of inlet gas ports and an outlet gas port, each inlet gas port being adapted to be in fluid communication with a supply of a desired gas;

b. at least one flow valve, each flow valve defining a passage through which a gas traverses, each flow valve being disposed adjacent to and in fluid communication with one respective inlet gas port of the plenum;

c. at least one flow controlling means for adjusting the passage of the flow valves, each flow controlling means being adapted to adjust the passage of one flow valve to change the gas flow rate therethrough;

d. an oxygen sensor, disposed in fluid communication with the outlet gas port of the plenum, for measuring the percentage composition of oxygen exiting from the plenum, wherein the oxygen sensor generates an output based on the measured percentage composition of oxygen;

e. a microprocessor for controlling the percentage composition of oxygen exiting from the plenum, the microprocessor being electrically coupled to the output of the oxygen sensor, wherein the microprocessor compares the output of the oxygen sensor to a predetermined level of oxygen, generates a response signal based on the comparison and communicates the response signal to at least one of the flow control means so that the percentage of oxygen in fluid communication with the output port of the plenum is maintained at the predetermined level; and f. a pressure sensor in fluid communication with the outlet gas port of the plenum, wherein the pressure sensor generates an output based on the pressure of the gases exiting the plenum, wherein the microprocessor is electrically coupled with and responsive to the output of the pressure sensor so that the microprocessor compares the output of the pressure sensor to a predetermined pressure and generates a response signal based on the comparison, and wherein the driver circuits adjust at least one flow controlling means in response to a signal from the microprocessor so that the pressure of the gases exiting from the plenum is maintained at the predetermined pressure.

* * * * *